(12) United States Patent
Socci

(10) Patent No.: US 7,976,827 B2
(45) Date of Patent: Jul. 12, 2011

(54) NAIL ENAMEL COMPOSITIONS HAVING A DECORATIVE COLOR EFFECT

(75) Inventor: Robert L. Socci, Cedar Grove, NJ (US)

(73) Assignee: Kirker Enterprises, Inc., Paterson, NJ (US)

( * ) Notice: Subject to any disclaimer, the term of this patent is extended or adjusted under 35 U.S.C. 154(b) by 1116 days.

(21) Appl. No.: 11/398,389

(22) Filed: Apr. 4, 2006

(65) Prior Publication Data

US 2007/0231281 A1   Oct. 4, 2007

(51) Int. Cl.
*A61K 8/00* (2006.01)
*A61K 8/18* (2006.01)

(52) U.S. Cl. .................................. 424/61; 424/400

(58) Field of Classification Search .................. None
See application file for complete search history.

(56) References Cited

U.S. PATENT DOCUMENTS

| | | |
|---|---|---|
| 3,864,294 A | 2/1975 | Busch, Jr. |
| 3,875,950 A | 4/1975 | Gens |
| 4,438,140 A | 3/1984 | Guillon et al. |
| 4,482,538 A * | 11/1984 | Davies ............................ 424/61 |
| 4,492,686 A | 1/1985 | Guillon et al. |
| 4,495,172 A | 1/1985 | Orlowski et al. |
| 4,740,370 A | 4/1988 | Faryniarz et al. |
| 4,749,564 A | 6/1988 | Faryniarz et al. |
| 4,822,423 A | 4/1989 | Soyama et al. |
| 4,832,944 A | 5/1989 | Socci et al. |
| 5,071,639 A | 12/1991 | Soyama et al. |
| 5,133,966 A | 7/1992 | Khamis |
| 5,143,723 A | 9/1992 | Calvo et al. |
| 5,324,506 A | 6/1994 | Calvo et al. |
| 5,486,354 A | 1/1996 | Defossez et al. |
| 5,612,021 A | 3/1997 | Mellul |
| 5,747,019 A | 5/1998 | Weisman |
| 5,792,447 A | 8/1998 | Socci et al. |
| 5,817,304 A | 10/1998 | Mondet et al. |
| 5,830,485 A | 11/1998 | Gueret et al. |
| 5,833,967 A | 11/1998 | Ramin |
| 5,851,517 A | 12/1998 | Mougin et al. |
| 5,863,523 A | 1/1999 | Socci et al. |
| 5,882,636 A | 3/1999 | Mui et al. |
| 5,935,590 A | 8/1999 | Razzano |
| 5,944,994 A | 8/1999 | Asher et al. |
| 5,954,871 A | 9/1999 | Nicolas-Morgantini et al. |
| 5,977,217 A | 11/1999 | Socci et al. |
| 5,989,575 A | 11/1999 | Razzano |
| 6,080,414 A | 6/2000 | Smith, III et al. |
| 6,083,491 A | 7/2000 | Mellul et al. |
| 6,123,951 A | 9/2000 | Gueret et al. |
| 6,136,300 A | 10/2000 | Ellingson et al. |
| 6,139,822 A * | 10/2000 | Socci et al. ...................... 424/61 |
| 6,190,682 B1 | 2/2001 | Razzano |
| 6,203,806 B1 | 3/2001 | Ramin et al. |
| 6,238,652 B1 | 5/2001 | Nastasi |
| 6,296,836 B1 | 10/2001 | Engler |
| 6,333,043 B1 | 12/2001 | Gueret et al. |
| 6,355,260 B1 | 3/2002 | Tanaka et al. |
| 6,367,484 B1 | 4/2002 | Ramin et al. |
| 6,432,209 B2 | 8/2002 | Sahbari |
| 6,432,417 B1 | 8/2002 | Mellul et al. |
| 6,447,761 B1 | 9/2002 | Ramin |
| 6,471,950 B1 | 10/2002 | Farer et al. |
| 6,500,439 B1 | 12/2002 | Morita et al. |
| 6,641,805 B1 | 11/2003 | Morita et al. |
| 6,696,049 B2 | 2/2004 | Vatter et al. |
| 6,705,327 B2 | 3/2004 | Tilson |
| 6,740,314 B2 | 5/2004 | Socci et al. |
| 6,811,770 B2 | 11/2004 | Ferrari et al. |
| 6,814,797 B2 | 11/2004 | Kaneko et al. |
| 6,875,245 B2 | 4/2005 | Pavlin |
| 6,886,710 B2 | 5/2005 | Verna et al. |
| 6,905,696 B2 | 6/2005 | Marotta et al. |
| 2002/0007768 A1 * | 1/2002 | Yoshimura et al. ............ 106/400 |
| 2002/0033117 A1 * | 3/2002 | Inoue et al. ................. 106/31.68 |

OTHER PUBLICATIONS www.FDA.GOV/ForIndustry/Coloradditives/coloradditiviesinventories/ucm115641.html. accessed Oct. 4, 2009 Summary of Color Additives for Use in United States in Foods, Drugs, Cosmetics, and Medical Devices.* www.FDA.gov. Summary of color additives for use in the united states in food, drus, cosmetics, and medical devices.*

* cited by examiner

*Primary Examiner* — Anand U Desai
*Assistant Examiner* — Melissa S Mercier
(74) *Attorney, Agent, or Firm* — Lerner, David, Littenberg, Krumholz & Mentlik, LLP

(57) ABSTRACT

A base coat nail enamel composition that forms a decorative color effect over natural or synthetic nails. The base coat nail enamel composition includes at least one dye in a sufficient amount, such that when a clear, tinted or pigmented top coat nail enamel composition is formed thereon, the combined base and top coat nail enamel compositions will exhibit a decorative effect by virtue of forming a different color than either the color of the base nail enamel composition or the top coat nail enamel composition.

17 Claims, No Drawings

NAIL ENAMEL COMPOSITIONS HAVING A DECORATIVE COLOR EFFECT

BACKGROUND OF THE INVENTION

Nail enamel compositions include a class of nail care products regularly used by women as part of their beauty care routine. These nail care products are available in a multitude of product formulations, from clears to infinite colors. Typically, clear nail enamel compositions include a film forming polymer, a film forming resin, a plasticizer and one or more solvents. In the case of a color nail enamel composition, the product may also include a thixotropic compound, a suspending agent and one or more pigments, or in the alternative, an organic coloring polymer may be used. In addition to these components, a number of optional and proprietary components are often included such as UV light absorbers, moisturizers, stabilizers, fragrances and the like.

Nail enamel compositions have heretofore been formulated to satisfy a number of highly desirable film forming properties. For example, desirable properties often include smoothness of application, rapid dry time, scratch resistance, detergent and oil resistance, lustrous appearance, wear and chip resistance and the like. Often most important, it has been highly desirable that the resulting nail enamel film be smooth and uninterrupted by imperfections, for example, orange peel effect, wrinkling, cracking, pitting, bubbling and the like. To this end, nail enamel compositions have included many different types of additives in order to improve the aforementioned desirable properties of the resulting film.

Despite the improved properties of the nail enamel film, the aesthetic or decorative appearance differed very little. In particular, manufacturers often times would produce nail enamel compositions having the same popular colors as their competitors. This provided little distinction between nail enamel products of different manufacturers to the ultimate consumer. Nail enamel compositions having a more decorative appearance were produced by including small pieces of light reflecting decorative material known as glitters within the composition. From the foregoing, it can be appreciated that the appearance of nail enamel compositions has differed very little over the years. To this end, the present invention provides a nail enamel composition which produces a film having a decorative effect heretofore unknown.

SUMMARY OF THE INVENTION

Accordingly, in one embodiment, there is described a base coat nail enamel composition including at least one dye in a sufficient amount, such that when a clear, tinted or pigmented top coat nail enamel composition is formed thereon, the combined base and top coat nail enamel compositions will exhibit a decorative effect by virtue of forming a different color than either the color of the base nail enamel composition or the top coat nail enamel composition.

In a preferred embodiment, the dye is added into the base coat nail enamel composition as a dry dye.

In another preferred embodiment, the base coat nail enamel composition further comprises at least one pigment.

In another embodiment, there is described a nail enamel composition comprising any one of the aforementioned base nail enamel compositions and a clear or tinted top coat nail enamel composition, in which the clear or tinted top coat nail enamel composition is formed over the base coat nail enamel composition.

In yet another embodiment, there is described a nail enamel kit for forming a decorative film over natural or synthetic nails, the kit comprising any of the aforementioned base coat nail enamel compositions, the base coat nail enamel composition forming a first film having a first color over the natural or synthetic nails, and a top coat nail enamel composition, the top coat nail enamel composition forming a second film having a second color over the first film. The combination of the first and second films results in a third color that is different from both the first and second colors.

In yet another embodiment, there is described a method of forming a decorative film over natural or synthetic nails, the method comprising applying any one of the aforementioned base coat nail enamel compositions over the natural or synthetic nails to form a first film having a first color and then, applying a top coat nail enamel composition over the base coat nail enamel composition to form a second film having a second color. The combination of the first and second films results in a third color that is different from both the first and second colors.

DETAILED DESCRIPTION

In describing the various embodiments of the present invention, specific terminology will be resorted to for the sake of clarity. However, the present invention is not intended to be limited to the specific terms so selected, and is to be understood that each specific term includes all technical equivalence which operate in a similar manner to accomplish a similar purpose.

The present invention broadly discloses base coat nail enamel compositions (hereinafter "base coats") which, when a clear, tinted or pigmented top coat nail enamel composition (hereinafter "top coat") is formed thereon, will exhibit a decorative effect by virtue of forming a different or altered color than both the color of the base coat and the color of the top coat. By the term "color," it is meant to encompass any tone or hue. In this regard, in addition to any tints and pigments, the term "color" also includes clear nail enamel compositions, coats and films. Thus, in the present invention, "clear" is also a color. By the term "clear," it is meant that the nail enamel composition does not contain a coloring agent or, at most, an incidental amount of a coloring agent. By the term "tint," it is meant that the nail enamel composition contains a minor amount of a coloring agent, such that the coloring agent imparts a light hue or shade to the top coat nail enamel. By the term "pigmented," it is meant that the nail enamel composition contains more than a minor amount of a colorant, such as a pigment, to impart a darker hue or shade. In all instances, the nail enamel composition may be either fully or partially transparent.

The base coats of the present invention are applied to natural or synthetic nails. Afterwards, a clear, tinted or pigmented top coat is applied over the base coats.

Nail enamel compositions can be formulated as a clear or color nail enamel composition. For base coats, they may further be formulated to be suitable for coating natural and synthetic nails. Typically, a clear nail enamel composition contains one or more film forming components, a plasticizer and one or more solvents. Clear nail enamel compositions may also include one or more thixotropic compounds. In the case of a color nail enamel composition, the composition will generally include a thixotropic compound, a suspending agent and one or more colorants, such as pigments. In addition to these compounds, a number of optionally and proprietary components may be included such as UV light absorbers, moisturizers, stabilizers, fragrances and the like. Typical nail enamel compositions are disclosed in U.S. Pat. No. 5,977,217, entitled Quick Drying Nail Enamel Composition, filed on Apr. 7, 1998 in the name of Socci, et al.; U.S. Pat. No. 5,863,523, entitled Nail Enamel Composition, filed on Dec. 10, 1996 in the name of Socci, et al.; and U.S. Pat. No. 5,792,447, entitled Nail Enamel Composition, filed on Nov. 15, 1996 in the name of Socci, et al., which patents are assigned to the same assignee of the present application, the disclosures of which are incorporated herein by reference.

Additionally, dyes have been used as colorants for nail enamel compositions. Dyes have long been distinguished from pigments. In particular, dyes are known as chemical compounds which exhibit their coloring power or tinctorial strength when dissolved in a solvent. On the other hand, pigments are insoluble colored materials which color by dispersion. For example, while dyes are generally soluble in solvents, such as water, propylene, glycol, glycerine, esters, alcohols and hydrocarbons, pigments and derivatives of pigments (such as lakes) are generally insoluble in most solvents.

In the present invention, one or more dyes are added to the base coat in an amount sufficient to enable a decorative effect when a clear, tinted or pigmented top coat is applied onto or formed on the base coat. The decorative effect may be in the form of a different or altered color for the final nail enamel composition (i.e., a base coat with a top coat formed thereon) or film than both the color of the base coat and the color of the top coat. Some characteristics of the color change or effect include, either singly or in some combination, a different hue, a different brightness, an increased intensity and higher saturation in color. The intensity and type of the color change or effect may vary depending upon various factors, including, but not limited to, the amount of dye used, the amounts and types of the other ingredients in the base and top coats, and whether the top coat is clear, tinted or pigmented. Although not bound by this theory, it is believed the color effect or change is at least partly attributable to the extra dye present in the base coat. With a higher amount or concentration of dye added to the base coat, after the solvent top coat is formed on the base coat, the solvent in the top coat solubilizes or further solubilizes the extra dye in the base coat, which results in the color effect or change.

The base coats according to the present invention contain one or more dyes. Any dye may be used as long as they are soluble in any solvent included in the base and top coats. The dyes for use in the present invention may include any of those dyes which are generally known for use in nail enamel compositions. These dyes may be organic or inorganic. Such dyes may include dyes that are certified by the Division of Color Technology of the United States Food and Drug Administration (FDA). Drug & Cosmetic (D&C) dyes are one category of dyes that are certified by the FDA. Examples of D&C dyes for use in the present invention include D&C Violet No. 2, D&C Green No. 5, D&C Green No. 6, D&C Orange No. 5, D&C Red No. 17, D&C Yellow No. 8, D&C Yellow No. 10 and D&C Yellow No. 11. The dyes for use in the present invention may be industrial dyes or metal complex dyes. Such dyes include any of the Colour Index (CI) dyes set forth by The Society of Dyers and Colourists. Examples of CI dyes for use in the present invention include Solvent Yellow 21, Solvent Yellow 62, Solvent Yellow 82, Solvent Yellow 90, Solvent Orange 45, Solvent Orange 54, Solvent Orange 58, Solvent Orange 60, Solvent Orange 99, Solvent Red 8, Solvent Red 89, Solvent Red 91, Solvent Red 119, Solvent Red 122, Solvent Red 124, Solvent Red 127, Solvent Red 132, Solvent Red 160, Solvent Red 218, Dye Salt, Basic Blue 7, Solvent Blue 48, Solvent Blue 70, Solvent Black 27, Solvent Black 28, Solvent Black 29 and Solvent Black 34.

Although the amount of dye in the compositions of the present invention will vary as a function of the type of dye and other components included in the composition, in general, the dyes are included in an amount of at least about 0.05% by weight of the composition, and more preferably between about 0.05% and about 1% of the composition.

The one or more dyes may be added in a solubilized form or in-solution, although in a preferred embodiment, the one or more dyes are added to the base coat in a dry form, as "dry dyes." By the term "dry dyes," it is meant that the dyes are either not solubilized, dissolved or otherwise in-solution when added to the nail enamel composition, or at most, partially solubilized. Typically, the dry dyes, when added to the base coat, are in a powder form.

In base and top coats according to the present invention, one or more pigments and a suspending agent may also be added. One or more known insoluble organic colorants which are well known in the nail enamel art may also be added to these compositions. Pigments are added to the composition to provide cosmetically acceptable shades and to pacify the films.

Pigments for use in the present invention may include any of those pigments which are generally known for use in nail enamel compositions. For example, these pigments can include cosmetic grade or purified titanium dioxide, yellow and red iron oxides, bismuth oxychloride, iron blue, iron black, mica particles, ultramarine blue, D&C Red #6, D&C Red #7, D&C Red #34, chromide oxide greens, carbon black, lampblack, aluminum powder and the like. Other pigments which may be used in compositions according to the present invention may include the Lake pigments, for example, FD&C Blue No. 1 Lake, FD&C Blue No. 2 lake, FD&C Red No. 40 Lake, FD&C Yellow No. 5 Lake, FD&C Yellow No. 6 Lake, FD&C Yellow No. 10 Lake, Amaranth Lake, Erythrosine Lake, Ponceau 4R Lake, Carmoisine Lake, D&C Red #6 barium Lake, D&C Red #7 calcium Lake and the like. In addition to the above named pigments, there may also be included titanated micas, polyethylene teraphthalates and pearl essence which is a suspension of crystalline guanine in nitrocellulose and solvents, as well as other additives which will affect the appearance of the pigment. Although the amount of pigment in the compositions of the present invention will vary as a function of the type of pigment and other components included in the composition, in general, pigments can be included in an amount up to about 10% by weight of the base coat and in an amount up to about 1% by weight of the top coat. Preferably, the amount of pigment included in a top coat is limited to about 0.1% or less by weight of the top coat.

When pigments are included in compositions according to the present invention, it is useful to include a suspending agent for enhancing the suspension of the pigments in the other components of the nail enamel composition. Although a number of suspending agents which are generally used in conventional nail enamel compositions may be used to produce compositions according to the present invention, preferred suspending agents include colloidal clays, montmorillonite clays, especially stearalkonium hectorite, stearalkonium bentonite, fumed silica, and mixtures thereof. The suspending agent is present in the compositions of the present invention in amounts sufficient to produce a gel, preferably a colloidal gel. In general, the suspending agent is included in the amount ranging from about 0.5% to about 3% by weight of the composition.

In addition to the above described components, the nail enamel compositions of the present invention may also include additional additives including stabilizers, thixotropic agents, UV light absorbers such as ectocrylene and benzophenone-1, fragrances, moisturizers and medicants, depending on the intended result. These components are well known in the art and may be included in amounts well within the teachings of the prior art.

Although the top coat of the present invention may include a color tint, as described above, the top coat is preferably clear, and include no coloring agent or an incidental amount of a coloring agent.

The nail enamel compositions of the present invention also include one or more solvents, such as those generally used in conventional nail enamel compositions. The solvents may be organic or inorganic. Examples of suitable solvents for use in the nail enamel compositions of the present invention include ethyl acetate, methyl acetate, ethanol, isopropanol, propyl acetate, n-butanol, xylene, DI acetone alcohol, aromatic (containing phenyl groups), amyl acetate, ethers, ketones, alkanes for example, pentane, cyclopentane, hexane, toluene, heptane, cyclohexane, cyclic ethers for example, tetrahydrofuran and 1,4-dioxane, cellosolve, butyl cellosolve acetate, cellosolve acetate, methyl cellosolve acetate, butyl cellosolve, ethyl cellosolve, phenylated solvents for example, xylene, esters of acetic acid for example, methyl acetate, ethyl acetate, n-butyl acetate, chlorinated hydrocarbons for example, methylene chloride, chloroform and methylchloroform. The aforementioned solvents can be used alone or in mixtures thereof. In general, the amount of solvent used in the compositions of the present invention range from about 60% to about 80% by weight of the composition, and preferably about 65% to about 75% by weight of the composition.

The nail enamel compositions may contain one or more film forming components such as film forming polymers, for example, cellulose acetate, cellulose acetate butyrate, ethyl cellulose, vinyl polymers, nitrocellulose, as well as acrylic type polymers, and mixtures thereof. Nitrocellulose provides an unusual combination of properties of toughness, durability, solubility and solvent release. Examples of nitrocellulose are the so called nitrocellulose RS ⅛ sec. and ¼ sec.; nitrocellulose RS ½ sec.; and nitrocellulose RS 5-6 sec. and 60-80 sec., which have higher viscosities than the earlier grades. The term "RS" refers to the brand of nitrocellulose with a nitrogen content of about 11.2 to about 12.8% with solubility in esters, ketones and glycol ethers manufactured by Hercules, Inc. The terms ⅛ sec., sec., ¼ sec., 5-6 sec., etc. represent viscosity and refer to the time it takes for a ball to fall to a given depth in the material. Nitrocellulose is typically supplied in 70% concentrations, wet with 30% ethyl or isopropyl alcohol. As used in the present application, the percentage of nitrocellulose in a given composition will be on a wet basis unless otherwise stated. Nail enamel compositions of the present invention may include the above film forming polymers and combinations thereof in an amount ranging from about 5% to about 25% by weight of the composition, and more preferably in the range of about 10% to about 15% by weight of the composition.

In addition to the aforementioned film forming polymers, the nail enamel compositions can also include one or more film forming resins. Exemplary film forming resins which may be used in the present invention either alone or in combination with the film forming polymers include, for example, drying and non-drying alkyd resins, polyvinyl resins for example polyvinyl acetate, polyester resins, epoxy resins, acrylic polymers and copolymers, maleic modified glycerol esters of rosin, and toluene sulfonamide/epoxy resins, i.e., tosylamide epoxy resins. It is also within the scope of the nail enamel compositions of the present invention to include aldehyde condensation products such as arylsulfonamide formaldehyde resins, i.e., tosylamide formaldehyde resins, specifically toluene sulfonamide formaldehyde resin which is a condensation product of formaldehyde and toluene sulfonamide. The amount of film forming resin and combinations thereof can range from about 2% to about 25% by weight of the composition, and preferably about 7% to about 12% by weight of the composition. Overall, the nail enamel compositions can include a number of film forming components in the overall range of from about 2% to about 25% by weight of the composition, and preferably about 10% to about 15% by weight of the composition.

The nail enamel compositions according to the present invention can also include one or more plasticizers to soften and plasticize particularly any film forming polymer present in the nail enamel composition. The plasticizer may be in either liquid or solid form, as well as combinations thereof. The plasticizers may be plasticizers known to be suitable for use in nail enamel compositions. Examples of such known plasticizers include tricresyl phosphate, dibutyl tartrate, benzyl benzoate, tributyl phosphate, butyl acetyl ricinoleate, butyl glycolate, butyl stearate, triphenyl phosphate, triethyl citrate, camphor, castor oil, esters of citric, stearate, phalic, oleic, phosphate, butyric and benzoic acid, glyceryl triacetate and glyceryl triproprionate, 2,2,4-trimethyl-1,3-pentandiiol diisobutyrate and mixtures thereof. The nail enamel compositions of the present invention also contemplate the use of phthalate type plasticizers, either alone or in combination with the aforementioned plasticizers, for example, diamylphthalate, dibutyl phthalate, diethyl phthalate, dioctyl phthalate, dibutoxy ethylphthalate and mixtures thereof.

Plasticizers included in the nail enamel compositions of the present invention are in amounts sufficient to provide acceptable flexibility to the nail enamel film on the human or synthetic nail surface. In this regard, the amount of plasticizer and combinations thereof for use in the nail enamel compositions of the present invention range from about 1% to about 20% by weight of the composition, and preferably about 5% to about 10% by weight of the composition.

The base and top coats in accordance with the present invention can be manufactured by thoroughly and intimately mixing together all the components in amounts described in accordance with the present invention. Examples of satisfactory equipment and how to use them are readily apparent to one of ordinary skill in the nail enamel art.

The following examples of base and top coat nail enamel compositions in accordance with the present invention are presented by way of illustration only. Examples 1 to 3 and 5 represent actual examples, and Example 4 represents a prophetic example. These examples are not intended to be limiting the present invention either as to the inclusion of a lesser number of components, the substitution of additional components or variations in the percentages of the range of components. In this regard, any range of numbers recited in the examples, specification or claims, such as that representing a particular set of properties, units of measure, conditions, physical states or percentages, is intended to literally incorporate expressly herein by reference or otherwise, any number falling within such range, including any subset of numbers within any range so recited. For example, whenever a numerical range with a lower limit and an upper limit is disclosed, any number falling within the range is specifically disclosed.

Also, the term "about" encompasses greater and lesser values than those specifically recited provided that the value of the relevant property or condition facilitates reasonably meeting the technologic objective(s) of the present invention as described in detail in the specification and claims. More specifically, the term "about" when used as a modifier for, or in conjunction with, a variable, is intended to convey that the numbers and ranges disclosed herein are flexible and that practice of the present invention by those skilled in the art using, for example, concentrations, amounts and contents that are outside of a stated range or different from a single value, will achieve the desired result, namely, a nail enamel composition, coat or film with a decorative color effect or color change effect, as described above.

EXAMPLE 1

BASE COAT WITH D&C VIOLET #2 DRY DYE

| INGREDIENT | WT/PERCENT |
|---|---|
| ETHYL ACETATE | 25.015 |
| BUTYL ACETATE | 24.300 |
| NITROCELLULOSE | 12.600 |
| PROPYL ACETATE | 10.300 |
| TOSYLAMIDE FORMALDEHYDE RESIN | 9.500 |
| ISOPROPYL ALCOHOL | 5.400 |
| TRIMETHYL PENTANYL DIISOBUTYRATE | 3.000 |
| TRIPHENYL PHOSPHATE | 3.000 |
| ETHYL TOSYLAMIDE | 1.500 |
| STEARALKONIUM BENTONITE | 1.000 |
| CAMPHOR | 1.200 |
| DIACETONE ALCOHOL | 0.800 |
| STEARALKONIUM HECTORITE | 0.300 |
| BENZOPHENONE-1 | 0.050 |
| CITRIC ACID | 0.030 |
| DIMETHICONE | 0.005 |
| D&C VIOLET #2 DYE | 1.000 |
| BISMUTH OXYCHLORIDE | 1.000 |

EXAMPLE 2

BASE COAT WITH D&C VIOLET #2 DRY DYE

| INGREDIENT | WT/PERCENT |
|---|---|
| ETHYL ACETATE | 25.515 |
| BUTYL ACETATE | 24.300 |
| NITROCELLULOSE | 12.600 |
| PROPYL ACETATE | 10.300 |
| TOSYLAMIDE FORMALDEHYDE RESIN | 9.500 |
| ISOPROPYL ALCOHOL | 5.400 |
| TRIMETHYL PENTANYL DIISOBUTYRATE | 3.000 |
| TRIPHENYL PHOSPHATE | 3.000 |
| ETHYL TOSYLAMIDE | 1.500 |
| STEARALKONIUM BENTONITE | 1.000 |
| CAMPHOR | 1.200 |
| DIACETONE ALCOHOL | 0.800 |
| STEARALKONIUM HECTORITE | 0.300 |
| BENZOPHENONE-1 | 0.050 |
| CITRIC ACID | 0.030 |
| DIMETHICONE | 0.005 |
| D&C VIOLET #2 DYE | 1.000 |
| ALUMINUM POWDER | 0.500 |

EXAMPLE 3

BASE COAT WITH INDUSTRIAL DRY DYE (Solvent Red 122)

| INGREDIENT | WT/PERCENT |
|---|---|
| ETHYL ACETATE | 41.400 |
| BUTYL ACETATE | 24.100 |
| SD ALCOHOL 40B | 9.700 |
| NITROCELLULOSE | 8.100 |
| ISOPROPYL ALCOHOL | 4.400 |
| AMYL ACETATE | 3.300 |
| SUCROSE ACETATE ISOBUTYRATE | 2.600 |
| ETHYL TOSYLAMIDE | 1.800 |
| CAMPHOR | 1.500 |
| STEARALKONIUM HECTORITE | 1.200 |
| DIACETONE ALCOHOL | 0.700 |
| PHOSPHORIC ACID | 0.030 |
| CITRIC ACID | 0.010 |
| DIMETHICONE | 0.010 |
| ALUMINUM POWDER | 0.050 |
| SAVINYL RED 4 GLS DYE (Solvent Red 122) | 0.650 |

EXAMPLE 4

BASE COAT WITH D&C RED 17 DYE SOLUTION

| INGREDIENT | WT/PERCENT |
|---|---|
| ETHYL ACETATE | 25.000 |
| BUTYL ACETATE | 24.000 |
| NITROCELLULOSE | 12.600 |
| PROPYL ACETATE | 2.415 |
| POLYESTER RESIN | 9.000 |
| T-5030 DYE 17 SOLUTION (1.0% SOLUTION IN BUTYL ACETATE) | 10.000 |
| TRIMETHYL PENTANYL DIISOBUTYRATE | 4.000 |
| TRIPHENYL PHOSPHATE | 4.000 |
| ETHYL TOSYLAMIDE | 0.500 |
| STEARALKONIUM BENTONITE | 1.000 |
| CAMPHOR | 1.000 |
| BENZOPHENONE-1 | 0.050 |
| CITRIC ACID | 0.030 |
| DIMETHICONE | 0.005 |
| BISMUTH OXYCHLORIDE | 1.000 |
| ISOPROPYL ALCOHOL | 5.400 |

EXAMPLE 5

TOP COAT

| INGREDIENT | WT/PERCENT |
|---|---|
| ETHYL ACETATE | 36.3190 |
| SD ALCOHOL 40B | 19.0000 |
| BUTYL ACETATE | 17.9500 |
| CELLULOSE ACETATE BUTYRATE | 11.9000 |
| ACRYLATES COPOLYMER | 3.9000 |
| TRIMETHYL PENTANYL DIISOBUTYRATE | 3.0000 |
| SUCROSE BENZOATE | 1.9400 |
| TRIPHENYL PHOSPHATE | 1.9400 |
| NITROCELLULOSE | 1.7500 |
| ETOCRYLENE | 1.0000 |
| ISOPROPYL ALCOHOL | 0.7500 |
| BENZOPHENONE-1 | 0.5000 |

-continued

| TOP COAT | |
|---|---|
| INGREDIENT | WT/PERCENT |
| DIMETHYL POLYSILOXANE | 0.0500 |
| D&C VIOLET #2 | 0.0010 |

The base and top coats, as described above, may be included in a nail enamel kit for forming a decorative film over natural or synthetic nails.

The aforementioned base and top coats produce a decorative film with a color change effect when applied to a natural or synthetic nail.

Initially, a natural or synthetic nail is coated with a base coat of the present invention. Depending upon the amount and types of colorants (e.g., dyes, pigments, solubilized dyes, lakes, etc.) included in the base coat, the applied base nail enamel composition will exhibit a certain color. Afterwards, a top coat is applied over the base nail enamel composition. It is contemplated that the top coat can be applied to also protect the base coat. The top coat may be either clear, tinted or pigmented, if so desired. To this end, there is known from the nail enamel art, as well as the examples disclosed herein, protective clear or tinted top coats which will form a protective continuous film.

The application of the top coat may take place immediately after application of the base coat over the natural or synthetic nail. In other words, the top coat can be applied while the base coat is still "wet." Alternatively, the base coat may be fully dry prior to application of the top coat. The base coat may even be allowed to partially dry, for example, to a condition known as "dry to touch." This condition arises when the surface of the resulting film may be touched with one's finger without leaving an impression of one's fingerprints. However, the film has yet to become completely dry. The time period to achieve a dry to touch will depend upon the particular base coat being used, the thickness of the coat applied, and temperature and humidity conditions. In short, the top coat may be applied at any time after the application of the base coat. However, preferably, the application of the top coat takes place when the base coat is "dry to touch."

The top coat is preferably applied over the base coat as a single coat. However, multiple coats may also be applied if so desired. Upon application of the top coat, the nail enamel composition of the combined base and top coats, while wet, when dry to touch and after fully dry, will exhibit a color change, in that the resulting color is different from both the color of the applied base coat and the color of the applied top coat. As described above, some characteristics of this color change or effect may include, either singly or in some combination, a different hue, a different brightness, an increased intensity and higher saturation in color.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A base coat nail enamel composition for forming a decorative film of a first color over a natural or synthetic nail, said composition comprising at least one film forming polymer soluble in an organic solvent, wherein said film forming polymer comprises nitrocellulose, at least one colored dye soluble in a first organic solvent within the base coat composition and soluble in a second organic solvent within a top coat composition, at least one first organic solvent capable of solubilizing said dye, and a plurality of colored particles present in the amount up to about 10% by weight of said composition which are generally insoluble in said first organic solvent, wherein at least a plurality of said colored particles are selected from the group consisting of titanium dioxide particles, aluminum particles and bismuth oxychloride particles; a suspending agent in a sufficient amount to produce a gel; wherein said dye is present in said base coat nail enamel composition in a sufficient amount whereby only upon application of at least one top coat nail enamel composition of a second color including at least one second organic solvent capable of solubilizing said dye in said base coat nail enamel composition results in a combination of said decorative film and said top coat nail enamel composition having a third color different from said first and second colors, wherein said color change is a difference in hue, brightness, intensity, saturation or a combination thereof between a first color of said base coat nail enamel composition and a second color of said decorative film after application of said top coat nail enamel composition to said base coat nail enamel composition.

2. The base coat nail enamel composition of claim 1, wherein said at least one dye is incorporated into said base coat nail enamel composition as a dry dye.

3. The base coat nail composition of claim 2, wherein said dry dye is in powder form.

4. The base coat nail composition of claim 2, wherein said dry dye is at least partially solubilized.

5. The base coat nail enamel composition of claim 1, wherein said at least one dye is incorporated into said base coat nail enamel composition while in-solution.

6. The base coat nail enamel composition of claim 1, wherein said dye is a cosmetic dye.

7. The base coat nail enamel composition of claim 6, wherein said cosmetic dye is selected from Drug & Cosmetic (D&C) Violet No. 2, D&C Green No. 5, D&C Green No. 6, D&C Orange No. 5, D&C Red No. 17, D&C Yellow No. 8, D&C Yellow No. 10 and D&C Yellow No. 11.

8. The base coat nail enamel composition of claim 1, wherein said dye is an industrial dye.

9. The base coat nail enamel composition of claim 8, wherein said industrial dye is selected from Colour Index Nos. Solvent Yellow 21, Solvent Yellow 62, Solvent Yellow 82, Solvent Yellow 90, Solvent Orange 45, Solvent Orange 54, Solvent Orange 58, Solvent Orange 60, Solvent Orange 99, Solvent Red 8, Solvent Red 89, Solvent Red 91, Solvent Red 119, Solvent Red 122, Solvent Red 124, Solvent Red 127, Solvent Red 132, Solvent Red 160, Solvent Red 218, Dye Salt, Basic Blue 7, Solvent Blue 48, Solvent Blue 70, Solvent Black 27, Solvent Black 28, Solvent Black 29 and Solvent Black 34.

10. The base coat nail enamel composition of claim 1, wherein said dye is present in an amount of at least about 0.05% by weight of said composition.

11. The base coat nail enamel composition of claim 1, wherein said dye is present in an amount between about 0.05% and about 1% by weight of said composition.

12. The base coat nail enamel composition of claim 1, wherein said solvent is present in an amount between about 60% and about 80% by weight of said composition.

13. The base coat nail enamel composition of claim 12, wherein said solvent is present in an amount between about 65% and about 75% by weight of said composition.

14. The base coat nail enamel composition of claim 1, wherein said dye is present in an amount between about 0.05% and about 1% by weight of said composition and said solvent is present in an amount between about 60% and about 80% by weight of said composition.

15. The base coat nail enamel composition of claim 1, wherein said colored particles have a color different than the color of said colored dye.

16. The base coat nail enamel composition of claim 1, wherein said colored particles further include particles selected from the group consisting of insoluble organic colorants, mica particles and pearl essence particles.

17. The base coat nail enamel composition of claim 1, wherein said second color is not clear.

* * * * *